United States Patent
Deng et al.

(10) Patent No.: US 9,180,318 B2
(45) Date of Patent: Nov. 10, 2015

(54) STABLE ORAL CARE COMPOSITIONS

(75) Inventors: Yan Deng, Shanghai (CN); Xiaoke Li, Shanghai (CN); ZhiQing Zhang, Shanghai (CN); GuoQing Zhao, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/580,745

(22) PCT Filed: Feb. 18, 2011

(86) PCT No.: PCT/EP2011/052453
§ 371 (c)(1),
(2), (4) Date: Aug. 23, 2012

(87) PCT Pub. No.: WO2011/110414
PCT Pub. Date: Sep. 15, 2011

(65) Prior Publication Data
US 2012/0315228 A1    Dec. 13, 2012

(30) Foreign Application Priority Data

Mar. 9, 2010  (WO) ............... PCT/CN2010/000286

(51) Int. Cl.
| A61Q 11/00 | (2006.01) |
| A61K 8/24  | (2006.01) |
| A61K 8/25  | (2006.01) |
| A61K 33/06 | (2006.01) |
| A61K 8/36  | (2006.01) |
| A61K 8/365 | (2006.01) |

(52) U.S. Cl.
CPC . *A61Q 11/00* (2013.01); *A61K 8/24* (2013.01); *A61K 8/25* (2013.01); *A61K 8/36* (2013.01); *A61K 8/365* (2013.01); *A61K 2800/31* (2013.01)

(58) Field of Classification Search
USPC ................... 424/49, 57, 401; 433/215, 216
See application file for complete search history.

(56) References Cited

U.S. PATENT DOCUMENTS

| 4,083,955 A | 4/1978 | Grabenstetter et al. |
| 4,565,691 A | 1/1986 | Jackson |
| 4,582,701 A | 4/1986 | Piechota, Jr. |
| 4,647,451 A | 3/1987 | Piechota, Jr. |
| 5,135,738 A | 8/1992 | Gaffar |
| 5,145,668 A | 9/1992 | Chow |
| 5,302,374 A | 4/1994 | Wagner |
| 5,571,502 A * | 11/1996 | Winston et al. ............ 424/52 |
| 5,603,922 A | 2/1997 | Winston |
| 5,605,675 A | 2/1997 | Usen |
| 5,614,175 A | 3/1997 | Winston |
| 5,817,296 A | 10/1998 | Winston |
| 5,879,663 A | 3/1999 | Nakabayashi |
| 5,958,380 A | 9/1999 | Winston |
| 6,010,684 A | 1/2000 | Wiedemann |
| 6,159,448 A | 12/2000 | Winston |
| 6,214,321 B1 | 4/2001 | Lee |
| 6,346,235 B1 | 2/2002 | Joziak |
| 6,485,708 B1 | 11/2002 | Winston |
| 8,257,721 B2 | 9/2012 | Butler |
| 2002/0006386 A1 | 1/2002 | Ibsen |
| 2002/0044910 A1 | 4/2002 | Johansen |
| 2004/0022746 A1 | 2/2004 | Fisher |
| 2004/0047814 A1 * | 3/2004 | Xu et al. ............ 424/49 |
| 2004/0101493 A1 | 5/2004 | Scott |
| 2005/0220724 A1 | 10/2005 | Busch |
| 2006/0110340 A1 | 5/2006 | Tung |
| 2007/0098652 A1 | 5/2007 | Chow |
| 2007/0183984 A1 | 8/2007 | Haas |
| 2007/0218017 A1 | 9/2007 | Busch |
| 2007/0254260 A1 | 11/2007 | Alden, IV |
| 2008/0213197 A1 | 9/2008 | Busch |
| 2008/0241797 A1 | 10/2008 | Busch |
| 2008/0292565 A1 | 11/2008 | Ting |
| 2009/0264291 A1 | 10/2009 | Soudant |

FOREIGN PATENT DOCUMENTS

| CN | 101428153 |  | 5/2009 |
| CN | 101428153 | A | 5/2009 |
| CN | 101600442 |  | 12/2009 |
| CN | 101600442 | A | 12/2009 |
| DE | 3942643 | B4 | 3/2008 |
| EP | 0206991 | A2 | 12/1986 |
| EP | 1566166 | A1 | 8/2005 |
| FR | 2287234 |  | 10/1975 |
| FR | 2287234 | A1 | 10/1975 |
| GB | 1516525 |  | 7/1978 |
| JP | 2001172147 |  | 6/2001 |
| JP | 2001172147 | A | 6/2001 |

(Continued)

OTHER PUBLICATIONS

Crick et al., Preparation and Characterisation of Super-Hydrophobic Surfaces, Chemistry A European Journal, 2010, pp. 3568-3588, vol. 16.

Li et al., What do we need for a superhydrophobic surface? A Review on the recent progress in the preparation of superhydrophobic surfaces, Chem. Soc. Rev., 2007, pp. 1350-1368, vol. 36.

Pang et al., Electrochemical synthesis of ordered alumina nanowire arrays, J Solid State Electrochem, 2003, pp. 334-347, vol. 7.

(Continued)

*Primary Examiner* — Lezah Roberts
(74) *Attorney, Agent, or Firm* — Greenberg Traurig, LLP

(57) ABSTRACT

A single-phase oral care composition is described. The composition comprises both calcium and phosphate sources and is substantially free of water and is substantially free of generated calcium phosphate comprising compounds. The single-phase oral care composition is stable, maintains good viscosity characteristics and avoids the need for compartmentalized packaging.

17 Claims, 5 Drawing Sheets

(56) References Cited

FOREIGN PATENT DOCUMENTS

| | | | |
|---|---|---|---|
| JP | 2001247439 | | 9/2001 |
| JP | 2001247439 | A | 9/2001 |
| WO | WO9204006 | | 3/1992 |
| WO | WO2008015117 | A2 | 2/2008 |
| WO | WO2008/068247 | * | 6/2008 |
| WO | WO2008068149 | A1 | 6/2008 |
| WO | WO2008068248 | A1 | 6/2008 |
| ZA | 9106570 | | 4/1992 |

OTHER PUBLICATIONS

Roach et al., Progress in superhydrophobic surface development, Soft Matter, 2008, pp. 224-240, vol. 4.

Weidemier, Ownership of University Inventions: Practical Considerations, iP Handbook, ., ., 5.4.

PCT International Search Report in PCT application PCT/EP2011/052453 dated Dec. 23, 2011 with Written Opinion.

\* cited by examiner

Insoluble calcium source and anhydrous oral care composition after 3 months storage at 50°C Oral Care Composition with Soluble Calcium Source SEM Images of Tooth Surface a b c d Anhydrous and hydrous oral care composition comparison Light reflection increased with 1μm hydroxyapatite layer formation Hydroxyapatite Formation

STABLE ORAL CARE COMPOSITIONS

FIELD OF THE INVENTION

The present invention is directed to a stable oral care composition. More particularly, the invention is directed to an oral care composition that results in remineralisation and whitening of teeth by delivering calcium and phosphate sources to the teeth of consumers when, for example, brushing teeth (i.e., in situ). The composition is surprisingly stable notwithstanding the fact that both calcium and phosphate sources are present in a single-phase composition. Moreover, the composition maintains good taste, texture and viscosity characteristics even when formulated as an anhydrous product.

BACKGROUND OF THE INVENTION

Many products we consume have a negative impact on our teeth. Acidic drinks and sweets, for example, can result in tooth erosion by attacking enamel that coats and protects the teeth. Moreover, foods and beverages we consume, like tomato sauce, berries, beets, soda or pop, coffee and tea can stain teeth and thereby result in a smile that is not bright and white. Tobacco based products and certain medications can also lead to teeth that look yellow or even brown.

Products that address tooth decay and/or whitening have been developed. Such products often comprise peroxides, abrasives or both in order to clean and whiten teeth. These types of products are often not desired since they do not contribute to the remineralisation of teeth and can cause damage to our teeth and gums if overused.

Aqueous-based products for whitening teeth have been described (e.g., commonly owned application WO 2008/068248) with water insoluble calcium salt and a source of phosphate ions. These products require the calcium source to be stored in a compartmentalized first composition and the phosphate source to be stored in a compartmentalized second composition that is separate and distinct from the first. The separation of such components or compositions prevents interaction between calcium and phosphate (and the formation of calcium and phosphate comprising compounds within the product) thereby maintaining the remineralisation and whitening efficacy of the products. Unfortunately, however, such dual compartmentalized products may not always be easy for the consumer to use and may require packaging that can be costly to the consumer, complex and environmentally unfriendly.

It is of increasing interest to develop an oral care product suitable to deliver calcium and phosphate sources to teeth (i.e., in-situ) whereby the product comprises both a calcium and phosphate source that may be delivered to teeth in a single-phase, free of compartmentalized packaging. This invention, therefore, is directed to a single-phase composition comprising calcium and phosphate sources. The composition is, unexpectedly, stable and has good taste, texture and viscosity characteristics even in the absence of water. The composition, unexpectedly, is substantially free of generated calcium and phosphate comprising compounds until the composition is applied to teeth and/or utilized in the oral cavity. Moreover, the single-phase composition of this invention surprisingly results in excellent remineralisation and whitening of teeth notwithstanding the fact that a calcium and phosphate source are present together in one phase prior to use.

ADDITIONAL INFORMATION

Efforts have been disclosed for making oral care products. In WO 2008/068149 A1 and WO 2008/068248 A1, oral care products with calcium and phosphate are described.

Other efforts have been disclosed for making oral care products. In U.S. Pat. Nos. 4,083,955, 5,605,675 and 6,214,321 B1, processes and compositions for remineralising dental enamel are described.

Still other efforts have been disclosed for making oral care compositions. In U.S. patent application Ser. No. 2009/0264291 A1, compositions and methods for preventing or reducing plaque and/or gingivitis using a bioactive glass containing dentifrice are described.

None of the additional information above describes a stable oral care composition comprising a water insoluble and/or slightly soluble calcium source and a phosphate source in a single-phase composition having good taste, texture and viscosity characteristics as claimed herein. Moreover, none of the additional information describes a single-phase composition that surprisingly results in excellent remineralisation and whitening of teeth notwithstanding the fact that a calcium and phosphate source are present together in one phase prior to use.

SUMMARY OF THE INVENTION

In a first aspect, the present invention is directed to a single-phase oral care composition comprising:
(a) a water insoluble and/or slightly soluble calcium source;
(b) a phosphate source;
(c) thickener; and
(d) carrier humectant wherein the oral care composition is suitable to remineralise and whiten teeth and is substantially free of water and generated calcium and phosphate comprising compounds.

In a second aspect, the present invention is directed to a packaged oral care product comprising the single-phase oral care composition of the first aspect of this invention.

In a third aspect, the present invention is directed to a method for remineralising and whitening teeth with the composition of the first aspect of this invention.

All other aspects of the present invention will more readily become apparent upon considering the detailed description and examples which follow.

Soluble and insoluble calcium source, as used herein, refers to the solubility of the calcium source in water. Soluble means a source that dissolves in water to give a solution with a concentration of at least 0.1 moles per liter at room temperature. Insoluble means a source that dissolves in water to give a solution with a concentration of less than 0.001 moles per liter at room temperature. Slightly soluble, therefore, is defined to mean a source that dissolves in water to give a solution with a concentration of greater than 0.001 moles per liter at room temperature and less than 0.1 moles per liter at room temperature. Oral care composition means a composition suitable for use in veterinary and/or human oral cavity applications but especially for use in human oral cavity applications. Substantially free of, as used herein, means less than 1.5%, and preferably, less than 1.0%, and most preferably, from 0.0 to 0.75% by weight, based on total weight of the oral care composition, including all ranges subsumed therein. Remineralisation, as used herein, means the in situ generation of hydroxyapatite on teeth to reduce the likelihood of tooth decay and improve the appearance of teeth by whitening through the generation of such new hydroxyapatite. Single-phase composition means a one phase composition having both calcium and phosphate sources therein and prior to dispensing or unpackaging and use. Anhydrous, as used herein, means substantially free of water. Generated calcium and phosphate comprising compound means a compound with calcium and phosphate like calcium phosphate and hydroxyapatite that is formed within the monophase product from distinct compounds comprising calcium and phosphate. Composition as used herein means, for example, paste, powder, gel, liquid (like mouthwash), spray, foam, balm, carried on a mouthstrip or a buccal adhesive patch, chewable tablet (or pastille), lozenge, cream or a strip of gum, but preferably, a paste like toothpaste. Oral care, as used herein means providing a benefit in the mouth and especially to the teeth.

All ranges defined herein are meant to include all ranges subsumed therein unless specifically stated otherwise. Comprising, as used herein, is meant to include consisting essentially of and consisting of.

BRIEF DESCRIPTION OF THE DRAWINGS

The subject matter which is regarded as the invention is particularly pointed out and distinctly claimed in the concluding portion of the specification. The invention, however, may be best understood by reference to the following description taken in conjunction with the accompanying drawing figures in which:

DETAILED DESCRIPTION OF THE PREFERRED EMBODIMENTS

Figure 1:
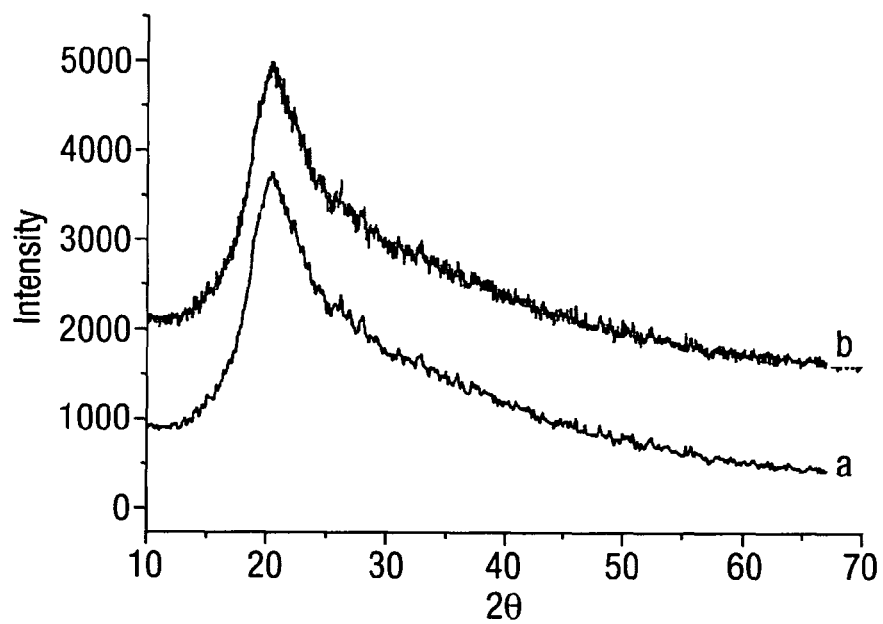
FIG. 1 shows x-ray defraction (XRD) peaks comparing anhydrous oral care compositions made according to this invention.

The calcium source suitable for use in this invention is limited only to the extent that the same may be used in an oral cavity. In a preferred embodiment, the calcium source employed is insoluble or slightly soluble in water, but most preferably, insoluble in water.

Illustrative examples of the types of calcium source that may be used in this invention include, for example, calcium phosphate (i.e., added), calcium gluconate, calcium oxide, calcium lactate, calcium carbonate, calcium hydroxide, calcium sulfate, calcium carboxymethyl cellulose, calcium alginate, calcium salts of citric acid, calcium silicate, mixtures thereof or the like. In a preferred embodiment the calcium source is calcium silicate. In a more preferred embodiment, the calcium silicate used is ($CaS_xO_3$) whereby the same is made commercially available under the name Microcal ET by Ineos Silicas, Ltd.

In yet another preferred embodiment, the calcium source is insoluble calcium silicate, present as the composite material calcium oxide-silica ($CaO—SiO_2$) as described in commonly-owned application Publication No. 2008/015117.

When a calcium silicate composite material is employed, the ratio of calcium to silicon (Ca:Si) may be from 1:10 to 3:1. The Ca:Si ratio is preferably from 1:5 to 2:1, and more preferably, from 1:3 to 2:1, and most preferably, from about 1:2 to 2:1. The calcium silicate may comprise mono-calcium silicate, bi-calcium silicate, or tri-calcium silicate whereby ratios of calcium to silicon (Ca:Si) should be understood to be atom ratios.

The calcium source employed in this invention may be in a crystalline or amorphous state, and preferably, the same is in an amorphous state. In an often preferred embodiment, the calcium source is in a mesoporous state, i.e. the source is a material having pores with diameters from 1 nm to 50 microns. Mesoporous calcium silicate (MCS) is often preferred.

The MCS which may be used in this invention can be made by combining a calcium salt, a silica precursor like silicate and a structure-directing agent to yield a solid suitable for calcinating. A more detailed description of the process that may be conducted to make the MCS suitable for use in this invention is described in the aforementioned commonly-owned application, Publication No. WO 2008/015117.

The amount of calcium source in the single phase composition of this invention is typically from 0.1 to 50%, and preferably, from 1 to 30%, and most preferably, from 5 to 20% by weight of the oral care composition based on total weight of the oral care composition and including all ranges subsumed therein.

The phosphate source that may be used in this invention is limited only to the extent that the same may be used in a composition suitable for use in an oral cavity. Illustrative examples of the types of phosphate source suitable for use in this invention include monosodium phosphate, sodium dihydrogen phosphate, disodium hydrogen phosphate, sodium pyrophosphate, tetrasodium pyrophosphate, sodium tripolyphosphate, sodium hexametaphosphate, potassium dihydrogenphosphate, trisodium phosphate, tripotassium phosphate, mixtures thereof or the like. The phosphate source is preferably one which is water soluble.

Typically, the phosphate source makes up from 0.5 to 15%, and preferably, from 2 to 12%, and most preferably, from 4 to 9% by weight of the oral care composition, based on total weight of the oral care composition and including all ranges subsumed therein. In a preferred embodiment, the phosphate source used is one which results in an oral care composition having a pH from 5.5 to 8, preferably from 6 to 7.5, and most preferably, about neutral. In a most preferred embodiment, the phosphate source used is trisodium phosphate and monosodium dihydrogen phosphate at a trisodium phosphate to monosodium dihydrogen phosphate weight ratio of 1:4 to 4:1, preferably 1:3 to 3:1, and most preferably, from 1:2 to 2:1, including all ratios subsumed therein.

The oral care compositions described herein may comprise ingredients which are common in the art, such as:

antimicrobial agents, e.g. Triclosan, chlorhexidine, copper-, zinc- and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds such as 2,2' methylenebis-(4-chloro-6-bromophenol);

anti-inflammatory agents such as ibuprofen, flurbiprofen, aspirin, indomethacin, etc.;

anti-caries agents such as sodium trimetaphosphate and casein;

plaque buffers such as urea, calcium lactate, calcium glycerophosphate and strontium polyacrylates;

vitamins such as Vitamins A, C and E;

plant extracts;

desensitizing agents, e.g. potassium citrate, potassium chloride, potassium tartrate, potassium bicarbonate, potassium oxalate, and potassium nitrate;

anti-calculus agents, e.g. alkali-metal pyrophosphates, hypophosphite-containing polymers, organic phosphonates and phosphocitrates, etc.;
biomolecules, e.g. bacteriocins, antibodies, enzymes, etc.
flavors, e.g., peppermint and spearmint oils;
proteinaceous materials such as collagen;
preservatives;
opacifying agents;
coloring agents like FD&C blue, yellow and/or red dyes/colorants;
pH-adjusting agents;
sweetening agents;
surfactants, such as anionic, nonionic, cationic and zwitterionic or amphoteric surfactants (e.g., sodium lauryl sulfate, sodium dodecylbenzene sulfonate);
particulate abrasive materials such as abrasive silicas, aluminas, calcium carbonates, zirconium silicate, polymethylmethacrylate, dicalciumphosphates, calcium pyrophosphates, hydroxyapatites, trimetaphosphates, insoluble hexametaphosphates as well as agglomerated particulate abrasive materials;
fluoride sources like sodium fluoride, stannous fluoride, sodium monofluorophosphate, zinc ammonium fluoride, tin ammonium fluoride, calcium fluoride, cobalt ammonium fluoride or mixtures thereof;
polymeric compounds which can enhance the delivery of active ingredients such as antimicrobial agents can also be included. Examples of such polymers are copolymers of polyvinylmethylether with maleic anhydride and other similar delivery enhancing polymers, e.g., those described in DE-A03,942,643;
buffers and salts to buffer the pH and ionic strength of the oral care compositions; and
other optional ingredients that may be included are, e.g., bleaching agents such as peroxy compound, e.g., potassium peroxydiphosphate, effervescing systems such as sodium bicarbonate/citric acid systems, color change systems, and the like.

Such ingredients common in the art typically and collectively make-up less than 20% by weight of the oral care composition, and preferably, from 0.0 to 15% by weight, and most preferably, from about 0.01 to about 12% by weight of the oral care composition, including all ranges subsumed therein.

Thickener may also be used in this invention and is limited only to the extent that the same may be added to a composition suitable for use in an oral cavity. Illustrative examples of the types of thickeners that may be used in this invention include, sodium carboxymethyl cellulose, hydroxyl ethyl cellulose, methyl cellulose, ethyl cellulose, gum tragacanth, gum Arabic, gum karaya, sodium alginate, carrageenan, guar, xanthan gum, Irish moss, starch, modified starch, silica based thickeners including silica aerogels, magnesium aluminum silicate (i.e., Veegum) Carbomers (cross-linked acrylates) and mixtures thereof.

Typically, sodium carboxymethyl cellulose and/or Carbomers are preferred. When a Carbomer is employed, those having a molecular weight of at least 700,000 are desired, and preferably, those having a molecular weight of at least 1,200,000, and most preferably, those having a molecular weight of at least about 2,500,000 are desired. Mixtures of Carbomers may also be used herein.

In an especially preferred embodiment, the Carbomer is Carbopol® 980. It has been described as a high molecular weight and cross-linked polyacrylic acid and identified via CAS number 9063-87-0. The same is available commercially from Lubrizol Advanced Materials, Inc.

Thickener typically makes up from 0.01 to about 10%, and preferably, from 0.1 to 8%, and most preferably, from 1.5 to 6% by weight of the oral care composition, based on total weight of the oral care composition and including all ranges subsumed therein.

When the oral care composition of this invention is a toothpaste or gel, the same typically has a viscosity from about 50,000 to 180,000 centipoise, and preferably, from 60,000 to 170,000 centipoise, and most preferably, from 65,000 to 165,000 centipoise, taken at room temperature with a Brookfield Viscometer, Spindle No. 4.

Suitable carrier humectants are preferably used in the oral care composition of the present invention and they include, for example, glycerin, sorbitol, propylene glycol, dipropylene glycol, diglycerol, triacetin, mineral oil, polyethylene glycol (preferably, PEG-400), alkane diols like butane diol and hexanediol, ethanol, pentylene glycol, or a mixture thereof. The carrier humectants should, in any case, be substantially free of water, and preferably, anhydrous. The same, for example, can be used in solid form, whereby glycerin is the preferred carrier humectant.

The carrier humectant is used to take the balance of the compositions up to 100%, and the same may be present in the range of from 10 to 90% by weight of the oral care composition. Preferably, the carrier humectant makes up from 25 to 80%, and most preferably, from 45 to 70% by weight of the oral care composition, based on total weight of the oral care composition and including all ranges subsumed therein.

The compositions of this invention are prepared by conventional methods of making oral care formulations. Such methods include mixing the ingredients under moderate shear and atmospheric pressure. The compositions are used in the oral cavity, and preferably, are of the form that may be brushed onto teeth with a toothbrush. Unexpectedly, the stable oral care compositions of this invention result in remineralisation of teeth (i.e., new hydroxyapatite formation) and teeth whitening. Typically, use (for a period of about two weeks to one month) of the stable oral care composition of the present invention will result in a new hydroxyapatite layer on teeth that is from 0.5 to 20 microns, and preferably, from 0.75 to 5 microns, including all ranges subsumed therein.

In toothpaste or gel form, the composition may be packaged in a conventional plastic laminate, metal tube or a single compartment dispenser. The same may be applied to dental surfaces by any physical means, such as a toothbrush, fingertip or by an applicator directly to the sensitive area. Solid dosage form types include pastilles, lozenges, chewing gums, tablets, mouthstrips, balms, and the like. These may be contained in art recognized packaging desirable for consumer use.

The following examples are provided to facilitate an understanding of the present invention. The examples are not provided to limit the scope of the claims.

Example 1

Oral care compositions (monophase) were prepared by mixing (in weight percent) the following ingredients under moderate shear until a homogeneous composition was obtained. Sample 3 is an aqueous-based control. Samples 1 and 2 were made consistent with the invention herein.

|  | Sample | | |
|---|---|---|---|
| Ingredient | 1 | 2 | 3 |
| Glycerin | Balance | Balance | — |
| $T_iO_2$ | 1 | 0 | — |
| Calcium silicate* | 15 | 15 | 15 |
| Silica abrasive | 8 | 8 | 8 |
| Trisodium phosphate | 3.8 | 3.8 | 3.8 |
| Monosodium dihydrogen phosphate | 3.2 | 3.2 | 3.2 |
| Sodium monofluorophosphate | 1.1 | 1.1 | 1.1 |
| Sodium lauryl sulfate (70%) | 2.2 | 2.2 | 7.3 |
| Flavor | 1 | 1 | 1.2 |
| Carbopol 980 | 0.3 | 0.3 | — |
| Silica thickener | 3 | 2 | 5 |
| Sorbitol (70%) | — | — | Balance |
| Water | — | — | 15.6 |
| Sweetener | — | — | 0.27 |
| Blue Covarine | — | — | 0.014 |
| Sodium carboxymethyl cellulose | — | — | 0.5 |

*$Ca_2S_iO_3$

The anhydrous oral care compositions made according to this invention were assessed for stability after storing the same for 3 months at 50° C. After 3 months of storage, the compositions were subjected to XRD characterization to assess if a chemical reaction took place between any calcium salt and phosphate salt formulated in the composition. Upon looking for characteristic peaks of calcium phosphate, the obtained XRD peaks (FIG. 1) showed that Sample 2 (when tested after 3 months storage at 50° C.) had an XRD peak that was about the same as the peak obtained for a freshly made single-phase oral care composition (consistent with this invention) in that no calcium phosphate peaks were detected. The results show that the insoluble calcium salt used in the present invention did not react with phosphate in the anhydrous oral care product after storage to generate calcium and phosphate comprising compounds. The control, Sample 3, displayed calcium phosphate generation after only one day of storage at 50° C.

The texture and taste of the oral care compositions made according to this invention were also assessed (after storage under the aforementioned conditions) by visually observing and using the compositions to brush teeth with a toothbrush. No graininess (e.g., precipitate), flavor loss or texture loss was detected in the compositions of Samples 1 and 2. The viscosity of Sample 1, measured at room temperature, was 140,000 cps. When extruded onto a smooth surface from a standard oral care tube, the resulting ribbon of composition maintained excellent shape and dimension characteristics and was suitable for use on a toothbrush.

The results herein unexpectedly show that the stability of the anhydrous oral care compositions of this invention is excellent since calcium and phosphate comprising compounds were not generated in the product. The stability of the compositions was also superior to that of the aqueous based control.

Example 2

Oral care compositions were prepared by mixing (in weight percent) the following ingredients under moderate shear until a homogeneous composition was obtained.

| Oral care composition - calcium source, water soluble | |
|---|---|
| Ingredient | Content (wt. %) |
| Glycerin | Balance |
| Sodium monofluorophosphate | 1.1 |
| Silica abrasive | 8 |
| Trisodium phosphate | 3.8 |
| Sodium dihydrogen phosphate | 3.2 |
| Calcium nitrate* | 15 |
| Sodium lauryl sulfate | 2.2 |
| Flavor | 1.2 |
| Silica thickener | 3.5 |

*$Ca(NO_3)_2 \cdot 4H_2O$

| Oral care composition - calcium source, water insoluble | |
|---|---|
| Ingredient | Content (wt. %) |
| Glycerin | Balance |
| Sodium monofluorophosphate | 1.1 |
| Silica abrasive | 8 |
| Trisodium phosphate | 3.8 |
| Sodium dihydrogen phosphate | 3.2 |
| Calcium silicate* | 15 |
| Sodium lauryl sulfate | 2.2 |
| Flavor | 1.2 |
| Silica thickener | 3.5 |

*$CaS_iO_3$

The stability of the oral care compositions prepared in this Example 2 was assessed after storage and via XRD.

Figure 2:
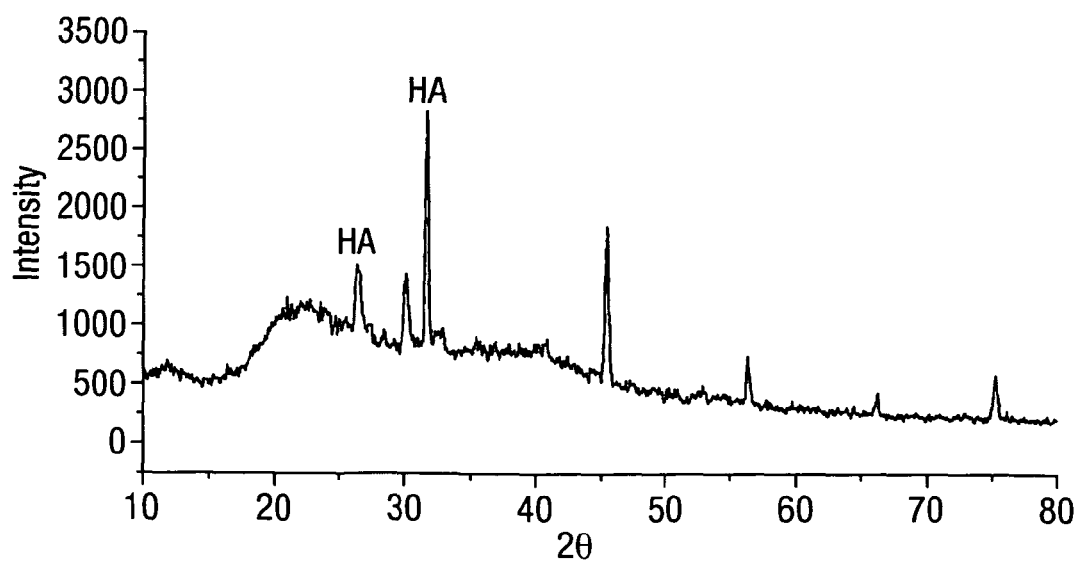
FIG. 2 shows an XRD pattern for an anhydrous oral care composition made with a soluble calcium source.

The XRD pattern of soluble calcium nitrate in the oral care composition (after two months of storage at 50° C.) revealed, as shown in FIG. 2, the generation of hydroxyapatite (HA).

The XRD pattern of insoluble calcium silicate in the oral care composition at the same temperature and after three months revealed no formation of hydroxyapatite. The results unexpectedly reveal that an insoluble calcium source is more stable than a soluble calcium source in an anhydrous composition, and therefore, leaving more available calcium for hydroxapatite formation at the surface of the teeth during an in situ application.

Example 3

Oral care compositions were prepared with soluble (Ca(NO_3)_2 4H_2O) and insoluble (CaS_iO_3) calcium sources as described in Example 2.

Extracted human cadaver teeth were cleaned using 75% alcohol and brushed using the compositions described herein with $Ca(NO_3)_2 \cdot 4H_2O$ and $CaS_iO_3$ as calcium sources. After 1 minute of brushing, the extracted teeth were cleaned with water and air dried. Scanning electron microscopy (SEM) was used to assess the deposition of calcium on the teeth. Results unexpectedly revealed that significantly more calcium deposited on the surface of the teeth when a composition with the water insoluble calcium source was used. The calcium deposition observed was calcium silicate, the same bonded to surface of the teeth via in situ formed calcium phosphate. For the composition with a water soluble calcium source, only a trace amount of calcium comprising particles were observed on the surface of the teeth assessed. Commercially available oral care compositions (i.e., silica abrasive comprising toothpastes) were also assessed and they resulted in small amounts of non-calcium based particles depositing on the surface of the teeth assessed. Therefore, it can be concluded that the compositions made according to this invention result in better whitening and remineralisation of teeth than conventional compositions and compositions having a soluble calcium source.

Figure 3:
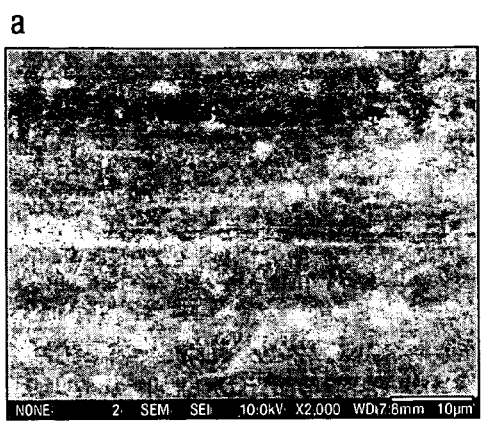
FIG. 3 shows scanning electron microscopy (SEM) images which identify calcium deposition on the surface of teeth.
Figure 3:
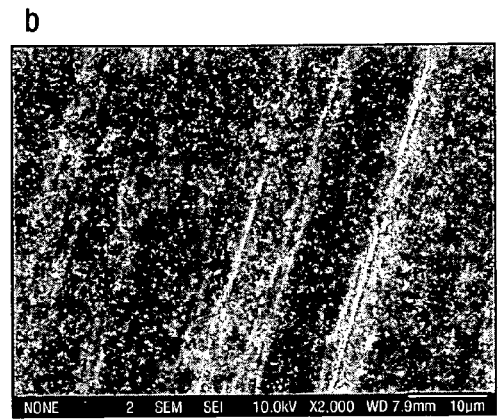
Figure 3:
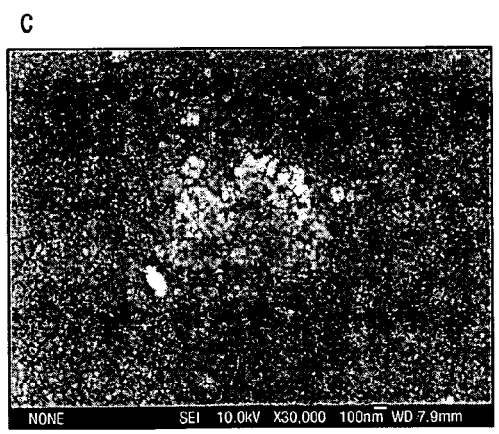
Figure 3:
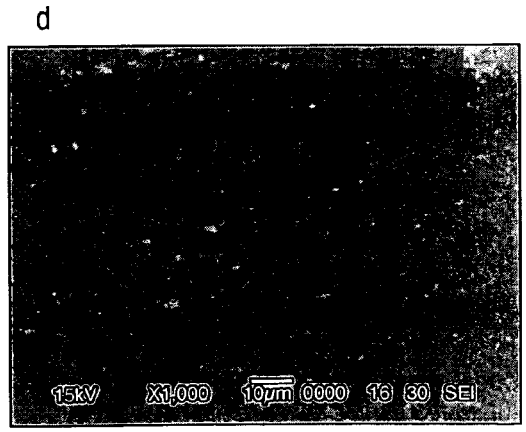

The SEM images of FIG. 3 show the surfaces of teeth treated with the oral care compositions made in this Example. Image (a), with the little calcium deposition visible, is taken after using the composition with the water soluble calcium source. Images (b) and (c), displaying significant calcium deposition, were taken after using a composition with insoluble calcium. Image (d) shows essentially no calcium deposition on the teeth assessed when a conventional monophase toothpaste comprising a silica abrasive was used.

The images unexpectedly reveal excellent calcium deposition when utilizing oral care compositions made according to this invention.

Example 4

Figure 4:
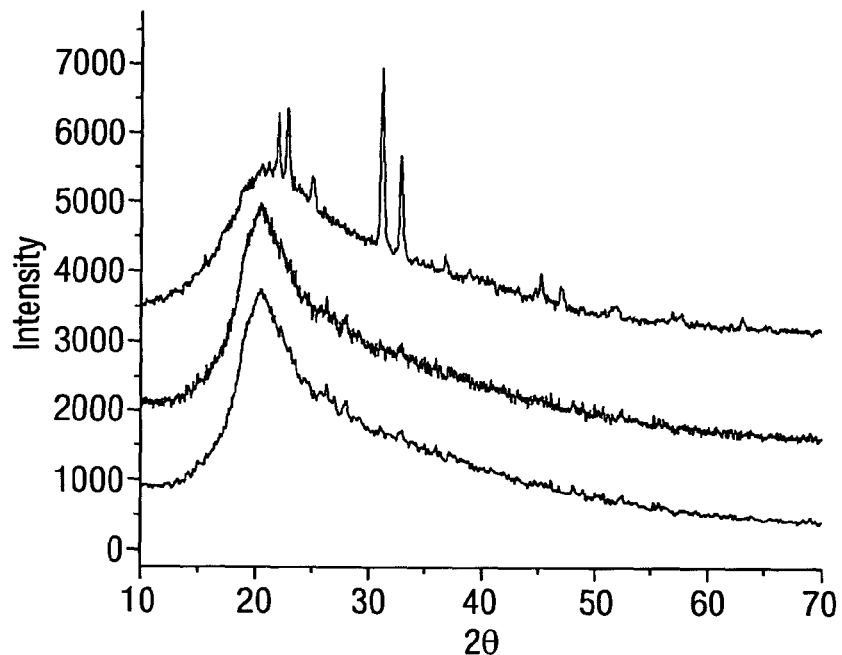
FIG. 4 shows XRD peaks comparing hydrous and anhydrous oral care compositions.

An oral care composition similar to the one described in Example 1 (Sample 1) was made except that 10% by weight sorbitol (30% $H_2O$) was used with glycerin. The stability of this composition was assessed by XRD after storage at 50° C. for one week. Characteristic peaks of hydroxyapatite were observed on the XRD pattern, indicating that the calcium silicate and sodium phosphate were not stable and generated calcium and phosphate comprising compounds when 3% water was formulated and present in the oral care composition. As shown in FIG. 4 at (c), the characteristic peaks of hydroxyapatite were high, indicating that large amounts of hydroxyapatite were formed in the product with 10% sorbitol. Anhydrous product, as described in Example 1, Sample 1, was stable and surprisingly displayed no characteristic peaks of hydroxyapatite formation when freshly made (FIG. 4 at (a)) and after storage at 50° C. for three months (FIG. 4 at (b)).

Example 5

Oral care compositions similar to Samples 1 and 2 of Example 1 were prepared. The oral care compositions were assessed for in situ hydroxyapatite formation on the surface of teeth as follows:

Extracted human cadaver teeth were cleaned first by washing the same with a 75% ethanol wash and scraping to remove calculus or stains until there was no obvious surface dirt or stains left on the surface of the teeth. Seven tooth blocks were used in each group tested. All groups were well hydrated in water at least 1 day before testing. A slurry was prepared by quickly mixing the aforementioned oral care compositions and water at a weight ratio of 1:1 followed by immediate brushing of the blocks of teeth. About 2 grams of oral care composition was used in each assessment. The groups were brushed for 3 minutes with the slurry and rinsed with water. Subsequently, the groups were stored in 15 mL plastic tubes filled with 3 mL saliva and placed in a shaking incubator stabilized at 37° C. After 1 hour of storage, the groups of teeth were taken out, and brushed again in a similar fashion. This procedure was repeated about 28 times, to simulate typical consumer brushing (2 times per day, for 2 weeks). The human saliva used was collected from panellists. Calcium concentration of the saliva collected varied from 23 to 60 ppm and phosphorus concentration (present as phosphate ions) varied from 124 to 154 ppm.

After 2 weeks of brushing, the treated groups of teeth were embedded in epoxy resin, and then cut into thin slices (or cross-sections) with a diamond saw. The slices were subsequently polished with an alumina slurry. In order to observe the boundary of tooth enamel and new in situ formed hydroxyapatite, the slices were incubated in 0.1% citric acid solution for 8 minutes to expose the microstructure of the enamel in the teeth. After washing with water and drying at 50° C. for 24 hours, the cross-sections were observed under Scanning Electronic Microscopy (SEM) to assess how much of new enamel or hydroxyapatite layer had accumulated during the 2 week test.

Figure 5:
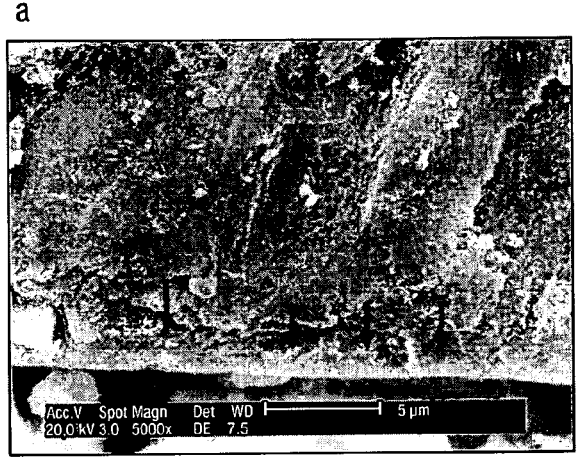
FIGS. 5*a*-5*c* show results associated with hydroxyapatite formation.
Figure 5:
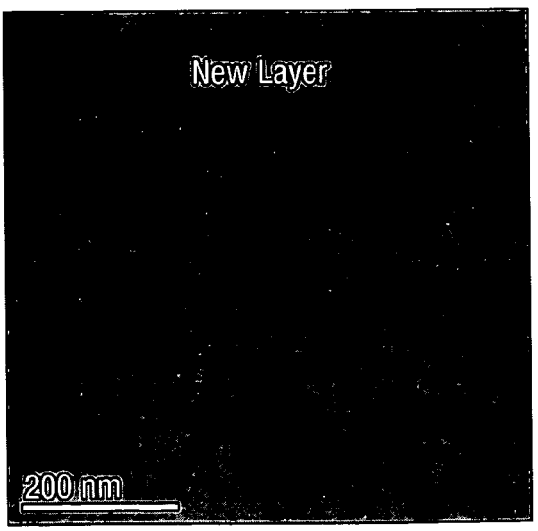
Figure 5:
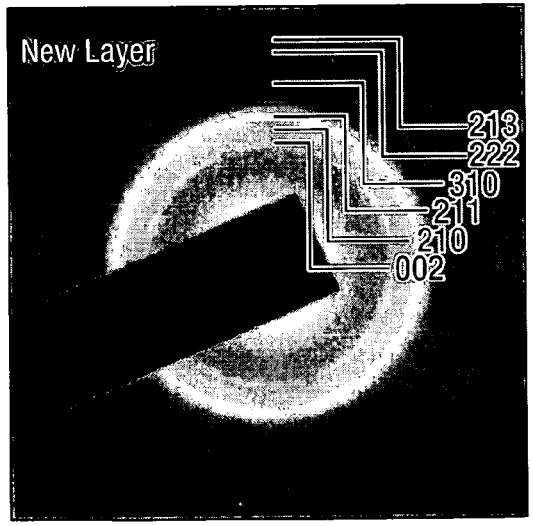

FIG. 5a shows the cross-section of teeth after the erosion with the citric acid. After SEM, it can be observed that the enamel of teeth is mainly composed by nanorod-like crystals that are highly organized into enamel prisms. However, such crystals are not observed in new hydroxyapatite formation. The resulting boundary between tooth enamel and the new hydroxyapatite is identified by the arrows in the figure. The thickness of the new hydroxyapatite layer is surprisingly about 1~3 μm after 2 weeks of treatment with the oral care composition of this invention.

Transmission election microscopy images of cross-sections of teeth treated with the oral care compositions of this example and invention were assessed as shown in FIG. 5b. Observed was the fact that the enamel of teeth is mainly composed by nanorod-like crystals, and however, such crystals are not observed in new hydroxyapatite formation on teeth. Elemental analysis using energy dispersive x-ray spectroscopy revealed that the composition was mainly composed of calcium phosphate and oxygen. The calcium/phosphate ratio was very close to that of typical tooth enamel. Selected area electron diffraction was also used to investigate the structure of the new hydroxyapatite layer as shown in FIG. 5c. The ring pattern was identified as the diffraction pattern of hydroxyapatite (0 0 2), (2 1 0), (2 1 1), (3 1 0), (2 2 2) and (2 1 3). Such results confirm the formation of hydroxyapatite.

Figure 6:
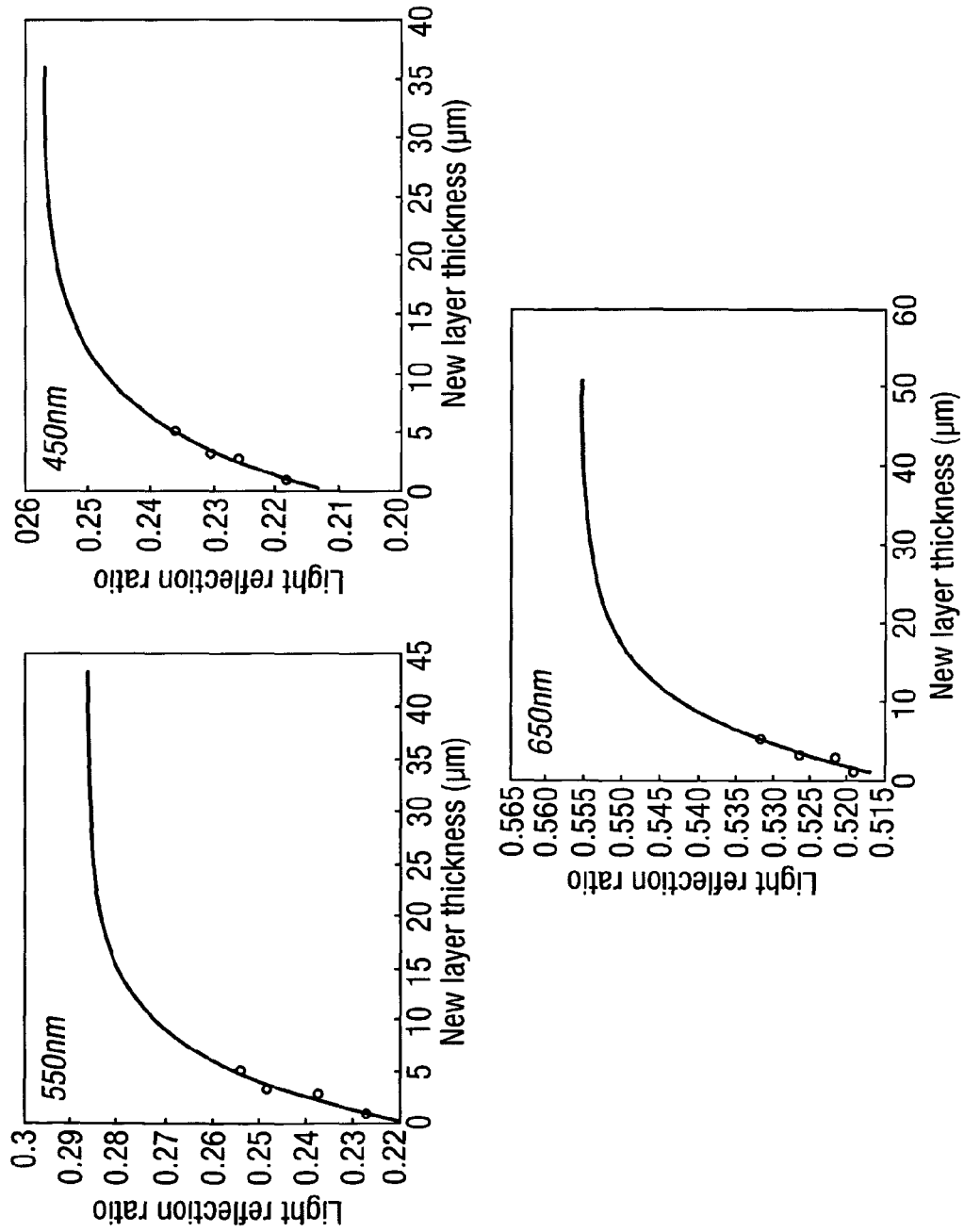

Newly formed hydroxyapatite layers increased light reflection, and such result was confirmed by measuring with a Colormeter (Color-Eye 7000A, X-rite). FIG. 6 reveals, at test points, that the light reflection increased with hydroxyapatite layer thickness at wavelengths of 450 nm, 550 nm and 650 nm (which represent blue, yellow and red light, respectively).

Figure 7:
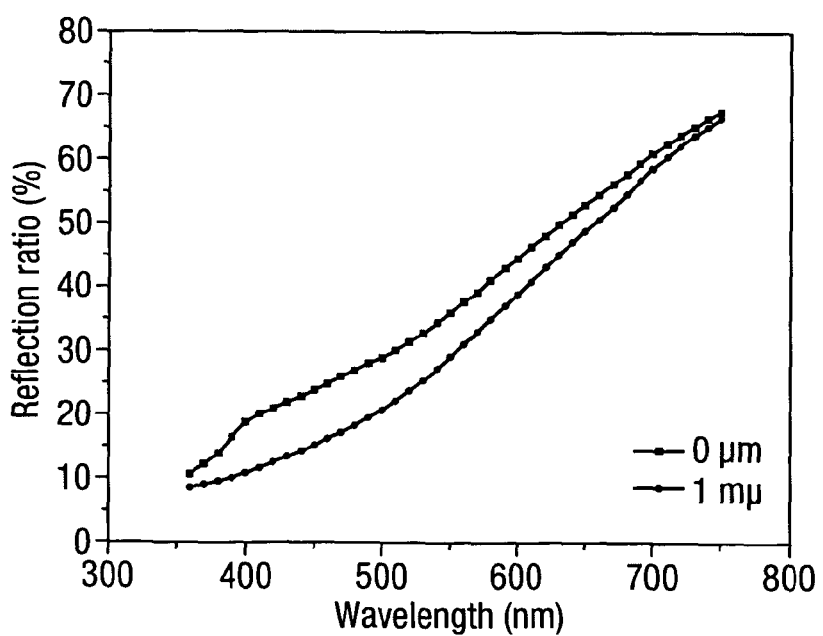
FIGS. 6 and 7 show light reflection and whiteness associated with hydroxyapatite formation on teeth.

FIG. 7 shows the full spectrum of light reflection on a tooth sample before and after new layer formation. The light reflection was thoroughly enhanced when a new hydroxyapatite layer with thickness of 1 μm formed on the surface of teeth. Such increase on light reflection results in whiter teeth.

The results show the monophase composition of the present invention unexpectedly yields whitening and remineralisation of teeth, a direct result of hydroxyapatite formation.

We claim:

1. An oral care composition comprising:
   (a) a calcium source having a solubility of less than 0.001 moles per liter of water at room temperature;
      wherein the solubility is measured by dissolving the calcium source in water and measuring the moles of the dissolved calcium source per liter of water at room temperature;
      wherein the calcium source is 0.1% to 50% by weight of the oral care composition;
   (b) a phosphate source;
      wherein the phosphate source is 0.5% to 15% by weight of the oral care composition;
   (c) thickener; and
   (d) carrier humectant
   wherein the oral care composition is toothpaste or gel;
   wherein the oral care composition comprises less than 1.5 wt % of water, based on a total weight of the oral care composition;

wherein the oral care composition is a one phase composition having the calcium source and the phosphate source therein; wherein the calcium source comprises at least one of calcium carboxymethyl cellulose, calcium alginate, calcium silicate and a mixture thereof; and wherein the oral care composition, when stored at 50 degrees Celsius for 2 months, is substantially free of calcium phosphate.

2. The composition according to claim 1 wherein the phosphate source, when dissolved in water at room temperature, forms a solution having a concentration of at least 0.1 moles per liter of water.

3. The composition according to claim 1 wherein the calcium source is a calcium silicate that has a Ca:Si ratio of 1:10 to 3:1.

4. The composition according to claim 1 wherein the phosphate source comprises at least one of monosodium phosphate, sodium dihydrogen phosphate, disodium hydrogen phosphate, sodium pyrophosphate, tetrasodium pyrophosphate, sodium tripolyphosphate, sodium hexametaphosphate, potassium dihydrogenphosphate, trisodium phosphate, tripotassium phosphate and a mixture thereof.

5. The composition according to claim 4 wherein the phosphate source comprises at least one of trisodium phosphate, disodium hydrogen phosphate, sodium dihydrogen phosphate, monosodium dihydrogen phosphate and a mixture thereof.

6. The composition according to claim 1 wherein the thickener is comprises at least one of carboxymethyl cellulose, hydroxyl ethyl cellulose, methyl cellulose, ethyl cellulose, gum tragacanth, gum Arabic, gum karaya, sodium alginate, carrageenan, guar, xanthan gum, Irish moss, starch, modified starch, silica based thickeners comprising at least one of silica aerogels, magnesium aluminum silicate, Carbomer and a mixture thereof.

7. The composition according to claim 6 wherein the thickener comprises at least one of carboxymethyl cellulose, Carbomer and a mixture thereof.

8. The composition according to claim 1 wherein the carrier humectant comprises at least one of glycerin, sorbitol, propylene glycol, dipropylene glycol, diglycerol, triacetin, mineral oil, polyethylene glycol, alkane diols like butane diol and hexanediol, ethanol, pentylene glycol and a mixture thereof.

9. The composition according to claim 1 wherein the oral care composition has a viscosity from 50,000 to 180,000 centipoise.

10. An oral care product comprising:
 (a) the oral care composition of claim 1; and
 (b) a single compartment package for storing the composition.

11. A method for whitening and/or remineralizing teeth comprising the step of contacting teeth with the oral care composition of claim 1.

12. The method according to claim 11 wherein the oral care composition is brushed onto the teeth.

13. The method according to claim 11 wherein the oral care composition results in obtaining a new layer of hydroxyapatite on tooth enamel, resulting in whiter teeth where the layer is from 0.5 to 20 microns thick.

14. An oral care composition comprising:
 (a) a calcium source;
  wherein the calcium source is 0.1% to 50% by weight of the oral care composition;
 (b) a phosphate source;
  wherein the phosphate source is 0.5% to 15% by weight of the oral care composition;
 (c) thickener; and
 (d) carrier humectant wherein the oral care composition is toothpaste or gel;
wherein the oral care composition comprises less than 1.5% of water, based on a total weight of the oral care composition;
wherein the oral care composition is a one phase composition having the calcium source and the phosphate source therein
wherein the calcium source comprises at least one of calcium carboxymethyl cellulose, calcium alginate, calcium silicate and a mixture thereof;
wherein the phosphate source comprises at least one of monosodium phosphate, sodium dihydrogen phosphate, disodium hydrogen phosphate, sodium pyrophosphate, tetrasodium pyrophosphate, sodium tripolyphosphate, sodium hexametaphosphate, potassium dihydrogenphosphate, trisodium phosphate, tripotassium phosphate and a mixture thereof; and
wherein the oral care composition, when stored at 50 degrees Celsius for 2 months, is substantially free of calcium phosphate.

15. The composition according to claim 14 wherein the calcium source is a calcium silicate.

16. The composition according to claim 15 wherein the calcium silicate has a Ca:Si ratio of 1:10 to 3:1.

17. The composition according to claim 14 wherein the phosphate source comprises at least one of trisodium phosphate, disodium hydrogen phosphate, sodium dihydrogen phosphate, monosodium dihydrogen phosphate and a mixture thereof.

* * * * *